United States Patent [19]

Steelman et al.

[11] 4,280,999

[45] Jul. 28, 1981

[54] INSECTICIDAL PROCESS UTILIZING CERTAIN URACILS

[75] Inventors: Carrol D. Steelman; Doyle M. Chambers; Michael D. Andis, all of Baton Rouge, La.

[73] Assignee: Louisiana State University Board of Supervisors, Baton Rouge, La.

[21] Appl. No.: 65,381

[22] Filed: Aug. 9, 1979

[51] Int. Cl.³ ............................................. A01N 43/54
[52] U.S. Cl. ................................................... 424/251
[58] Field of Search ......................................... 424/251

[56] References Cited

U.S. PATENT DOCUMENTS 3,235,357  2/1966  Loux ........................................ 71/92

OTHER PUBLICATIONS

Chemical Abstracts 83: 189318n, (1975).

Primary Examiner—Leonard Schenkman
Attorney, Agent, or Firm—Llewellyn A. Proctor

[57] ABSTRACT

A process for killing insects by applying to said insects and to substrates susceptable to infestation by said insects and their larvae an insecticidally effective amount of a composition containing at least one compound of the formula:

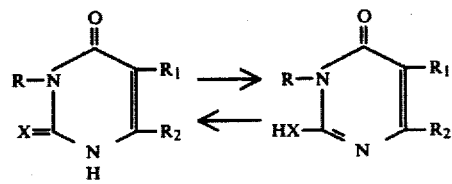

where:

R is alkyl of 1 through 10 carbon atoms, substituted alkyl of 1 through 8 carbon atoms, aryl of 5 through 10 carbon atoms, substituted phenyl, aralkyl of 5 through 13 carbon atoms, substituted aralkyl of 5 through 13 carbon atoms, alkenyl of 3 through 8 carbon atoms, alkynyl of 3 through 8 carbon atoms, cycloalkyl of 3 through 12 carbon atoms, cycloalkenyl of 4 through 12 carbon atoms, cycloalkyl alkyl of 4 through 13 carbon atoms, cycloalkenyl alkyl of 5 through 13 carbon atoms, (substituted cycloalkyl)alkyl of 5 through 14 carbon atoms, (substituted cycloalkenyl)alkyl of 5 through 14 carbon atoms, and cyano;

$R_1$ is chlorine, fluorine, bromine, iodine, methyl, ethyl, propyl, butyl, methoxy, ethoxy, propoxy, butoxy, nitro, alkoxymethyl of 2 through 6 carbon atoms, hydroxy alkyl of 1 through 6 carbon atoms, alkenyl of 3 through 6 carbon atoms, thiocyanato, cyano, thiolmethyl, alkylthio containing 1 through 4 carbon atoms, bromomethyl, methylthiomethyl, fluoromethyl, chloromethyl, phenylthiomethyl or carboxymethylthiomethyl;

$R_2$ is chloro, bromo, alkyl of 1 through 5 carbon atoms, chloroalkyl of 1 through 4 carbon atoms, bromoalkyl of 1 through 4 carbon atoms, or alkoxy of 1 through 5 carbon atoms; and X is oxygen or sulfur. These compounds have been found insecticidally active in low concentrations in the treatment of substrates which contain or are susceptible to infestation by insects and their larvae, particularly Diptera, and more particularly mosquitoes. These compounds can be formulated and applied as a solution, aerosol, powder or as an admixture of substances within which the compound is dispersed in low concentration as an insecticidally effective ingredient.

7 Claims, No Drawings

INSECTICIDAL PROCESS UTILIZING CERTAIN URACILS

In terms of the number of species, their absolute numbers and wide distribution, insects are the most eminently successful of animals. The most numerous species are the orders Coleoptera (beetles), Lepidoptera (butterflies and moths), Hymenoptera (ants, bees, wasps, etc.) and Diptera (true flies). Insects are not only annoying to man, but many carry diseases which affect man and animals, particularly domestic and game animals which are important to man.

True flies include some of the most important of all disease vectors. Phlebotomus sandflies transmit Leishmania organisms which cause oriental sore and espundia; trypanosomes causing kala azar; Bartonella causes Carri6ns disease; and viruses causing sand fly fever. Simuliam carry onchocerciasis; tabanid flies, and various worms including those which cause loaiasis; tsetse flies, trypanosomes of sleeping sickness; and house flies which may spread typhoid fever, dysentery and chlora. Fleas are able to transmit plague and endemic typhus.

Among the mosquitoes (Culicidae), insects known throughout the world, Anopheles transmits malaria; Aedes transmits the viruses of dengue and yellow fever; Culex, and other genera, transmit the causative organism of filariasis; and are the cause of various viral illnesses including the encephalitides. The ecosystem defined as the rice growing regions of Louisiana, California, Arkansas, Mississippi and Texas produce many species and massive populations of mosquitoes. Their intensive breeding in this agroecosystem poses a menace, as well as a nuisance, not only to man but to his pastured domestic animals which they attack.

Albeit by far the majority of insects are believed to benefit man, directly or indirectly, the best known species are those considered injurious because they annoy and endanger man and animals important to man, or attack and destroy man's crops and plant products. The control of these harmful species of insects has continued to be the major objective of the applied fields of medical and veterinary entomology, and of agricultural and forest entomology, respectively.

It is, accordingly, the primary objective of the present invention to provide a process for the control of a major portion of a given population of insects, particularly Diptera.

A specific object is to provide a novel process useful for the control, and destruction of mosquitoes.

These and other objects are achieved in accordance with the present invention embodying novel compositions, and process for the treatment and control of insects or their larvae by contacting same, or substrates of same, with an insecticidally effective amount of said compositions. The compositions are characterized as solutions, aerosols, dispersions, powdered solids or admixtures of substances which contain at least one compound, or ingredient insecticidally active in low concentrations and represented by the formulas:

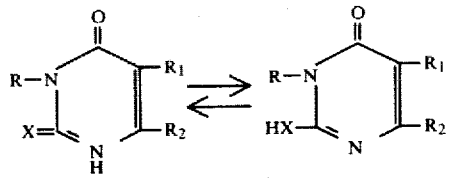

where:
R is alkyl of 1 through 10 carbon atoms, substituted alkyl of 1 through 8 carbon atoms, aryl of 5 through 10 carbon atoms, substituted phenyl, aralkyl of 5 through 13 carbon atoms, substituted aralkyl of 5 through 13 carbon atoms, alkenyl of 3 through 8 carbon atoms, alkynyl of 3 through 8 carbon atoms, cycloalkyl of 3 through 12 carbon atoms, cycloalkenyl of 4 through 12 carbon atoms, cycloalkyl alkyl of 4 through 13 carbon atoms, cycloalkenyl alkyl of 5 through 13 carbon atoms, (substituted cycloalkyl)alkyl of 5 through 14 carbon atoms, (substituted cycloalkenyl)alkyl of 5 through 14 carbon atoms, and cyano;

$R_1$ is chlorine, fluorine, bromine, iodine, methyl, ethyl, propyl, butyl, methoxy, ethoxy, propoxy, butoxy, nitro, alkoxymethyl of 2 through 6 carbon atoms, hydroxy alkyl of 1 through 6 carbon atoms, alkenyl of 3 through 6 carbon atoms, thiocyanato, cyano, thiolmethyl, alkylthio containing 1 through 4 carbon atoms, bromomethyl, methylthiomethyl, fluoromethyl, chloromethyl, phenylthiomethyl or carboxymethylthiomethyl;

$R_2$ is chloro, bromo, alkyl of 1 through 5 carbon atoms, chloroalkyl of 1 through 4 carbon atoms, bromoalkyl of 1 through 4 carbon atoms, or alkoxy of 1 through 5 carbon atoms; and X is oxygen or sulfur.

The salts of these compounds can also be used according to this invention. By "salts" is meant those compounds formed with such cations as sodium, potassium, lithium, calcium, magnesium, barium, strontium, iron, maganese and quaternary ammonium.

Some of the uracils of Formula 1 also form novel 1:1 addition compounds with nitrogenous bases. The exact structure of these compounds is not known. Although the compounds are, generally speaking, poorly soluble in water, they are, according to the best available information, believed to be essentially salt-like in structure. They will be symbolized by the following formula, with the understanding that it is representative only, and is not intended to illustrate actual structure:

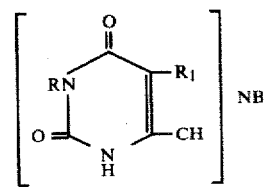

where:
R and $R_1$ are defined as in Formula 1, and NB is a nitrogenous base having an ionization constant $K_b$ of $\geq 10^{-9}$ in water.

Suitable nitrogenous bases are substituted, unsubstituted, cyclic and acyclic Amines, Amidines, and Guanidines. The amines can be primary, secondary or tertiary amines, polyamines, arylamines, or heterocyclicamines. Illustrative of such amines are: Sec-butylamine, 2-amino-2-methyl-1,3-propanediol, Trimethylenediamine, Ethanolamine, Dodecylamine, Ethylenediamine, Hexamethylenediamine, Cocoadiamine, Tallowdiamine, Hexamethyleneimine, Cyclohexylamine, Methoxpropylamine, Methylamine, Dimethylamine, Trimethylamine, Ammonia, Ethylamine, Propylamine, Butylamine, Octylamine, Pyridine, Piperidine, Tetramethylguanidine, Acetamidine, Benzylamine, Diethylenediamine, 2-aminobutanol-1, 2-aminooctanol-1.

Within the scope of Formula 1 is a group of novel compounds. These compounds are those of the formula:

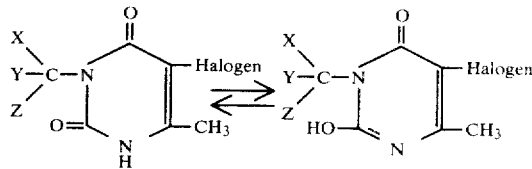

Where:
X is methyl or ethyl,
Y is hydrogen or methyl, and
Z is an alkyl group of 1 through 6 carbon atoms, and the salts of these compounds, as defined for Formula 1.

Certain 3,5,6-substituted uracils of Formula 1 also form water stable, novel complexes with phenol and substituted phenols. These complexes have the formula:

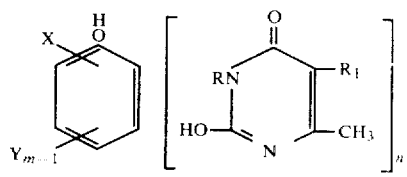

where:
R and $R_1$ are as defined in Formula 1,
X is hydrogen, chlorine, nitro, alkyl of 1 through 3 carbon atoms, bromine or —$OR_3$,
$R_3$ is alkyl of 1 through 3 carbon atoms,
Y is chlorine or alkyl of 1 through 3 carbon atoms,
m is a number 1 through 5, and
n is 1 or 2.

Preferred compounds are those of the formula:

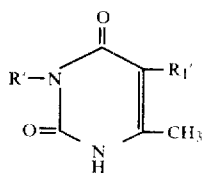

where:
R' is alkyl of 2 through 8 carbon atoms, substituted alkyl of 2 through 8 carbon atoms, phenyl, substituted phenyl, aralkyl of 5 through 10 carbon atoms, substituted aralkyl of 5 through 10 carbon atoms, cycloalkyl of 3 through 12 carbon atoms, cycloalkenyl of 5 through 12 carbon atoms, cycloalkyl alkyl of 4 through 13 carbon atoms, and (substituted cycloalkyl)alkyl of 5 through 14 carbon atoms; and $R_1'$ is chlorine, bromine, iodine, methyl, hydroxymethyl, methoxymethyl and nitro. The process is one which comprises contacting, or applying sufficient of one or more of said compositions to insects, or their larvae or to substrates containing said insects or their larvae, especially Diptera, and more especially mosquitoes to kill a major portion of a given population of the insects.

The insecticidally active ingredient has heretofore been recognized as a herbicide (U.S. Pat. Nos. 3,235,357 and 3,352,862; both of which are herewith incorporated by reference), but there heretofore appears to have been no recognition of the value of these compounds in small concentrations as effective insecticides. Illustrative of these species are: 3-(1-lower alkylethyl)-5-halogeno-6-methyluracils, 3-(2-lower alkylethyl)-5-halogeno-6-methyluracils, 3-(1-lower alkylisopropyl)-5-halogeno-6-methyluracils, 3-(cycloalkyl)-5-halogeno-6-methyluracils, 3-(cycloalkenyl)-5-halogeno-6-methyluracils, 3-(phenyl)-5-halogeno-6-methyluracils, 3-(bicycloalkyl)-5-halogeno-6-methyluracils, 3-(bicycloalkyl)-5halogeno-6-methyluracils, 3-(tricycloalkyl)-5-halogeno-6-methyluracils, 3-(tricycloalkenyl)-5-halogeno-6-methyluracils and the like, which are preferred. Specific compounds useful in the practice of this invention are: 5-bromo-3-sec-butyl-6-methyluracil, 5-bromo-3-sec-butyl-6-methyluracil, sodium salt, 5-chloro-3-sec-butyl-6-methyluracil, 5-bromo-3-tert-butyl-6-methyluracil, 5-chloro-3-tert-butyl-6-methyluracil, 5-bromo-3-(1-ethylpropyl)-6-methyluracil, 5-chloro-3-(1-ethylpropyl)-6-methyluracil, 5-bromo-3-isopropyl-6-methyluracil, 5-chloro-3-isopropyl-6-methyluracil, 5-chloro-3-cyclohexylmethyl-6-methyluracil, 3-cyclohexyl-5-methoxy-6-methyluracil, 3-sec-butyl-5,6-dimethyluracil, 5-bromo-6-methyl-5norbornylmethyluracil, 3-sec-butyl-6-methyl-5-nitrouracil, 3-cyclohexyl-5,6-dimethyluracil, 5-bromo-3-cyclohexyl-6-methyluracil, 5chloro-3-phenyl-6-methyluracil.

An insecticidally active compound, or compounds, is generally admixed with a liquid, suitably water, and dissolved therein to form an insecticidally active stock solution. Suitably, the active ingredient is added to the liquid, or to water in concentration ranging from about 50 parts to about 700 parts, preferably from about 400 parts to about 700 parts, based on a million parts by weight of the solution (ppm). Stock solutions, to which various other materials can be added if desired, can be used to form the insecticidally effective solutions, and the solutions can be applied to an insect infested substrate in concentrations that are lethal to the insect populations. The solutions applied to such insect infested substrate, however, need not be greater than that required to kill 90 percent of the insect population.

The compound is applied over an area which contains the insects, e.g., mosquitoes, in concentration sufficient to kill at least about 50 percent, and preferably about 90 percent of the population of insects which are to be destroyed. It has been found that a concentration of about 700 ppm of one of these compounds, or this concentration of the active ingredient contained in water, is adequate to kill at least about 90 percent of the mosquito larvae within the solution, or over an area within which the solution is in contact, within a twenty-four hour period.

It is also feasible to apply the insecticide as a formulated powdered solid, which contains the active ingredient, or an aerosol solution of the compound, or admixture of said compounds alone or with other ingredients can be sprayed over a geographical area, as from an aircraft, to provide the desired lethal concentration.

The following data shows the effectiveness of these compounds used as an insecticide in small concentrations for killing mosquito larvae collected from a Louisiana rice field. The tests employed are those employed by The World Health Organization, Annexes 2A and 2B (Wld Hlth Org. Techn, Rep. Ser., 170, No. 443) which were revised and combined as a result of discussions held at the WHO Expert Committee on Resistance of Vectors and Reservoirs to Pesticides which met in Geneva from 16 to 23 September 1975.

In order to demonstrate the effectiveness of these compounds, in low concentrations, 5-bromo-3-sec-butyl-6-methyluracil was dissolved in water and the solution employed to kill mosquitoes of the species *Culex pipiens quinquefasciatus.*

Sufficient mosquito larvae of the species *Culex pipiens quinquefasciatus* were obtained from a rice field to provide about 300 individual mosquitoes. The third or early fourth instar larvae were selected and retained initially in the water from which they were reared, those showing any abnormalities, such as a fuzzy appearance which might be indicative of parasites on the body surface were discarded. Lots of 20 to 25 of the healthy larvae were transferred, after washing to each of 24 small beakers, each containing 24 ml of water free of organic contaminants and traces of poisonous heavy metals.

Twenty-four larger glass vessels, 7.5 to 10 cm in diameter were then charged with 225 ml of water free of organic contaminants and trace amounts of poisonous heavy metals, this providing a water depth of 2.5 to 7.5 cm and a water volume of 250 ml. To each of the vessels of water, which was maintained at a temperature of about 25° C. throughout the tests, various concentrations of 5-bromo-3-sec-butyl-6-methyluracil was added by pipetting from a stock solution. Five concentrations and an untreated control each replicated 4 times were used to determine the lethal effects of the compound. Each of the vessels were then vigorously stirred for about 30 seconds to assure complete solution of the 5-bromo-3-sec-butyl-6-methyluracil within the water. Within 15 to 30 minutes after preparation 1.0 ml of each concentration and the mosquito larvae from each of the 24 small beakers were separately added to each of the 24 larger vessels. At the end of a 24 hour period a mortality count of the moribund and dead larvae in each vessel was made, and the percentage mortalities between 10 and 90 percent for each concentration was recorded. These data were then subjected to probit analyses to determine the concentration of the 5-bromo-3-sec-butyl-6-methyluracil required to cause 50 and 90% mortality.

The data showed that 400 parts of the 5-bromo-3-sec-butyl-6-methyluracil, in one million parts by weight of water, i.e., 400 ppm, was adequate to kill 50 percent of the mosquito larvae, and that 700 ppm of the 5-bromo-3-sec-butyl-6-methyluracil was sufficient to kill 90 percent of the larvae within the 24 hour period, as expressed in the table below.

TABLE

| Lethal Concentrations, PPM in Water Effective for Killing Culex Pipiens Quinquefasciatus | |
|---|---|
| $LC_{50}$ | $LC_{90}$ |
| 400 | 700 |

These compounds have also been found lethal to the larvae of mosquitoes of the species *Anopheles crucians, Anopheles quadrimaculatus, Culex erraticus,* and Psorphora columbiae.

These compounds have been found particularly effective in water management techniques where insecticidally effective amounts of the compound were added to the water used to flood rice fields. Various other means known to the art can also be employed in the treatment of various insect infested substrates. For example, the compounds can be blended with various other materials, admixtures, of solids powders, oil water emulsions within which the compound is blended, dispersions of the compound in various liquids, or solutions. Obviously, various modifications and changes can be made in the manner of application of the insecticide to various insect infested substrates, e.g., vegetation, soil, etc., without departing the spirit and scope of the present invention as well be apparent to those skilled in the art.

Having described the invention what is claimed is:

1. A process for killing insects by applying to said insects and to substrates susceptible to infestation by said insects or their larvae an insecticidally effective amount, but less than a herbicidally effective amount, of a compound which is selected from the group consisting of 5-bromo-3-sec-butyl-6-methyluracil, 5-bromo-3-sec-butyl-6-methyluracil, sodium salt, 5-chloro-3-sec-butyl-6-methyluracil, 5-bromo-3-tert-butyl-6-methyluracil, 5-chloro-3-tert-butyl-6-methyluracil, 5-bromo-3-(1-ethylpropyl)-6-methyluracil, 5-chloro-3-(1-ethylpropyl)-6-methyluracil, 5-bromo-3-isopropyl-6-methyluracil, 5-chloro-3-isopropyl-6-methyluracil, 5-chloro-3-cyclohexylmethyl-6-methyluracil, 3-cyclohexyl-5-methoxy-6-methyluracil, 3-sec-buty-5, 6-dimethyluracil, 5-bromo-6-methyl-3-norbornylmethyluracil, 3-sec-butyl-6-methyl-5-nitrouracil, 3-cyclo-hexyl-5, 6-dimethyluracil, 5-bromo-3-cyclohexyl-6-methyluracil and 5-chloro-3-phenyl-6-methyluracil.

2. The process of claim 1 wherein the compound is added to water in concentration from about 50 ppm to about 700 ppm.

3. The process of claim 2 wherein the concentration ranges from about 400 ppm to about 700 ppm.

4. The process of claim 1 wherein the compound is applied to a substrate in quantity sufficient to kill from about 50 percent to at least about 90 percent of the insects per acre of substrate.

5. The process of claim 1 wherein the compound constituting the active ingredient is dispersed in water in concentration ranging from about 400 ppm to about 700 ppm, and the water containing said compound is effective in killing mosquito larvae when standing in a flooded rice field.

6. The process of claim 5 wherein the water contains 5-bromo-3-sec-butyl-6-methyluracil.

7. The process of claim 5 wherein the mosquito larvae are of the species *Anopheles crucians, Anopheles quadrimaculatus, Clulex erraticus,* and *Psorophora columbiae.*

* * * * *